(12) United States Patent
Ullrich

(10) Patent No.: US 12,283,355 B2
(45) Date of Patent: *Apr. 22, 2025

(54) LOCATION-BASED ANTICIPATORY RESOURCE PROVISIONING

(71) Applicant: Meinhard Dieter Ullrich, Lexington, MA (US)

(72) Inventor: Meinhard Dieter Ullrich, Lexington, MA (US)

(73) Assignee: IMPRIVATA, INC., Waltham, MA (US)

( * ) Notice: Subject to any disclaimer, the term of this patent is extended or adjusted under 35 U.S.C. 154(b) by 284 days.

This patent is subject to a terminal disclaimer.

(21) Appl. No.: 17/833,006

(22) Filed: Jun. 6, 2022

(65) Prior Publication Data

US 2022/0301668 A1   Sep. 22, 2022

Related U.S. Application Data

(63) Continuation of application No. 16/846,759, filed on Apr. 13, 2020, now Pat. No. 11,380,428, which is a
(Continued)

(51) Int. Cl.
| | |
|---|---|
| *G06F 15/16* | (2006.01) |
| *G06F 3/0482* | (2013.01) |
| *G16H 10/60* | (2018.01) |
| *G16H 40/20* | (2018.01) |
| *G16H 40/67* | (2018.01) |
| *G16Z 99/00* | (2019.01) |
| *H04L 9/40* | (2022.01) |
| *H04L 67/12* | (2022.01) |
| *H04L 67/50* | (2022.01) |
| *H04L 67/52* | (2022.01) |

(Continued)

(52) U.S. Cl.
CPC ........... *G16H 10/60* (2018.01); *G06F 3/0482* (2013.01); *G16H 40/20* (2018.01); *G16H 40/67* (2018.01); *G16Z 99/00* (2019.02); *H04L 63/08* (2013.01); *H04L 67/12* (2013.01); *H04L 67/52* (2022.05); *H04L 67/535* (2022.05); *H04W 4/023* (2013.01); *H04W 4/029* (2018.02); *H04W 4/33* (2018.02); *H04W 64/00* (2013.01); *H04W 12/06* (2013.01); *H04W 12/63* (2021.01); *H04W 60/04* (2013.01)

(58) Field of Classification Search
None
See application file for complete search history.

(56) References Cited

U.S. PATENT DOCUMENTS

| | | |
|---|---|---|
| 8,141,075 B1 | 3/2012 | Chawla et al. |
| 8,607,067 B1 | 12/2013 | Jan van Rensburg et al. |

(Continued)

*Primary Examiner* — Nicholas R Taylor
*Assistant Examiner* — Ho T Shiu
(74) *Attorney, Agent, or Firm* — Morgan, Lewis & Bockius LLP

(57) ABSTRACT

In various embodiments, the predicted location of a user within an institutional space is associated with a node at or near that location, and a virtual desktop is prepared before a user has actually logged on and authenticated. Although users are not accorded access to applications and sensitive data until they have properly authenticated themselves, the virtual desktop and associated data are assembled and retrieved in the background in order to eliminate delay following log-on.

17 Claims, 3 Drawing Sheets

Related U.S. Application Data continuation of application No. 16/244,587, filed on Jan. 10, 2019, now Pat. No. 10,656,796, which is a continuation of application No. 14/945,658, filed on Nov. 19, 2015, now Pat. No. 10,216,366.

(60) Provisional application No. 62/183,793, filed on Jun. 24, 2015, provisional application No. 62/081,820, filed on Nov. 19, 2014.

(51) Int. Cl.

| | | |
|---|---|---|
| *H04W 4/02* | (2018.01) | |
| *H04W 4/021* | (2018.01) | |
| *H04W 4/029* | (2018.01) | |
| *H04W 4/33* | (2018.01) | |
| *H04W 12/63* | (2021.01) | |
| *H04W 64/00* | (2009.01) | |
| *H04W 12/06* | (2021.01) | |
| *H04W 60/04* | (2009.01) | |

(56) References Cited

U.S. PATENT DOCUMENTS

| | | |
|---|---|---|
| 10,216,366 B2 | 2/2019 | Ullrich |
| 10,656,796 B2 | 5/2020 | Ullrich |
| 10,917,788 B2 | 2/2021 | Slak et al. |
| 11,356,848 B2 | 6/2022 | Slak et al. |
| 11,363,424 B2 | 6/2022 | Ting et al. |
| 2005/0201345 A1* | 9/2005 | Williamson ........... G16H 40/63 370/338 |
| 2007/0167151 A1 | 7/2007 | Zinn et al. |
| 2010/0042994 A1 | 2/2010 | Vasilevsky et al. |
| 2012/0023223 A1 | 1/2012 | Branch et al. |
| 2012/0075061 A1 | 3/2012 | Barnes |
| 2013/0152047 A1 | 6/2013 | Moorthi et al. |
| 2013/0326510 A1 | 12/2013 | Adekile et al. |
| 2014/0095180 A1* | 4/2014 | Venkat ................ G06F 3/0233 705/2 |
| 2014/0200036 A1 | 7/2014 | Egner et al. |
| 2015/0049633 A1 | 2/2015 | Chen |
| 2015/0156081 A1 | 6/2015 | Chakra et al. |
| 2015/0172920 A1 | 6/2015 | Ben Ayed |
| 2015/0178459 A1 | 6/2015 | Wortman et al. |
| 2015/0200984 A1 | 7/2015 | Jung et al. |
| 2015/0339136 A1 | 11/2015 | Suryanarayanan et al. |
| 2015/0339628 A1 | 11/2015 | Oh et al. |
| 2016/0043968 A1 | 2/2016 | Jacob et al. |
| 2016/0080259 A1 | 3/2016 | Biancaniello |
| 2016/0142497 A1 | 5/2016 | Ullrich |
| 2019/0212882 A1 | 7/2019 | Ullrich |
| 2020/0310606 A1 | 10/2020 | Ullrich |

* cited by examiner

LOCATION-BASED ANTICIPATORY RESOURCE PROVISIONING

RELATED APPLICATION

This application is a continuation of U.S. patent application Ser. No. 16/846,759, filed Apr. 13, 2020, now U.S. Pat. No. 11,380,428, which is a continuation of U.S. patent application Ser. No. 16/244,587, filed Jan. 10, 2019, now U.S. Pat. No. 10,656,796, which is a continuation of U.S. patent application Ser. No. 14/945,658, filed Nov. 19, 2015, now U.S. Pat. No. 10,216,366, which claims the benefit of and priority to U.S. Provisional Patent Application Nos. 62/081,820, filed Nov. 19, 2014, and 62/183,793, filed Jun. 24, 2015, the entire disclosures of which are hereby incorporated by reference.

TECHNICAL FIELD

The invention relates generally to healthcare information technology, and in particular to systems and methods for location-based management of data, access control, and clinical collaboration.

BACKGROUND

In a busy healthcare environment, such as a hospital, clinicians roam frequently among patients, floors and buildings. Each time a clinician reaches a new location, she may require access to patient information or other medical data maintained by the facility (or elsewhere). That data may be accessed via a local, typically shared workstation, or via a handheld wireless device, such as a "smart phone" or tablet capable of hosting applications and establishing telecommunications, Internet and/or local intranet connections.

In particular, medical institutions from hospitals to physician practice groups to testing centers maintain diverse electronic medical records (EMR) systems, which collectively form the healthcare information backbone. EMR systems allow clinicians access to medical information maintained in various back-end systems. The typical workflow when a physician interacts with a patient involves first logging onto the computer system, then launching and logging into one or more EMR applications, selecting the right patient record, verifying that the record matches the patient, reviewing results (often from different sources), checking up on medical references, entering orders or prescriptions (e.g., using computerized physician order entry (CPOE) applications and ePrescribing), and/or charting patient progress. All of these activities may involve the same patient but different applications, and in some cases multiple separate applications for a single patient-specific activity.

Moreover, healthcare records are protected by strict privacy laws (such as the Health Insurance Portability and Accountability Act, or HIPAA), regulatory regimes, and institutional access policies. Accordingly, when a clinician moves from place to place, he may be required to log on to a new terminal or device, and because of data-access restrictions, the log-on procedure may involve cumbersome and/or multiple authentication modalities.

Thus, in a healthcare environment, where people move about frequently, a busy clinician may face delays as she moves from node to node. Even if the log-on procedure is automated and the clinician need not re-authenticate, restoring a previous session—i.e., re-launching applications, querying databases for previously requested patient data, etc.—can be time-consuming. Indeed, stringent security requirements may require re-authentication using a stronger modality even at the same node. For example, a properly authenticated user may need to re-authenticate when issuing an electronic prescription for a controlled substance, and to satisfy regulatory requirements that re-authentication may involve a "strong" modality such as a fingerprint or vein scan.

SUMMARY

Embodiments of the invention ease user interactions with local devices while maintaining a desired level of security, sparing the user the need to re-launch the applications that were running on the previously used device. In particular, knowledge of a user's (possibly changing) location is used to ease the burden of security compliance and session restoration. The user's location may be established based on the location of a currently stationary but movable device or by direct tracking, e.g., using "real-time location services" (RTLS).

In general, the applications active on a device are considered to define the user's "session" on the device. Although a session may be broadly viewed as involving both remotely hosted and purely local applications, the present invention is primarily concerned with the former—i.e., applications that may be remotely "provisioned" to the user via a virtual desktop. At the same time, it should be understood that some local applications can be replicated by remote hosting; that is, so long as an application is amenable to subsequent remote provisioning, it is immaterial for purposes of defining a "session" whether the application is currently being run locally (offline) or on a hosted basis.

In some embodiments, when the user leaves a node or logs off a current session, the session is stored for subsequent re-creation. In practice, this means that data sufficiently descriptive of the current user state is maintained to ease subsequent provisioning of the session on a different device. The degree of provisioning can range from re-launch of applications in use during the previous session to full re-creation of the session state prior to departure from the device or log-off, including retrieval of the data (e.g., the particular patient records or lab results being viewed in an EMR application).

Accordingly, in a first aspect, the invention relates to a method of anticipatory provisioning of resources for a mobile user in an institutional space. In various embodiments, the method comprises the steps of (a) providing a database storing records for a plurality of users, each of the records specifying, for one of the users, (i) data specifying a provisioning policy for the user including at least one location-based triggering event, (ii) data specifying session resources for the mobile user, and (iii) data indicative of a current location of the user; (b) in response to an electronically detected location-based triggering event of the mobile user and the provisioning policy stored in the database for the mobile user, causing a virtual desktop including the session resources specified for the mobile user to be created within a hosted session at a server; (c) receiving, at a network node, log-on credentials for the mobile user; and (d) upon acceptance of the log-on credentials, providing network-based access to the launched resources at the node.

In some embodiments, the location-based triggering event is detection of user presence at a first location, and the method further comprises predicting a second location for the mobile user, where the second location is based on and different from the first location; delivering a virtual desktop including the resources to a node at the second location; and providing network-based access to the virtual desktop by the mobile user at the node following log-on of the mobile user thereat.

The location-based triggering events causing the delivery of the virtual desktop for a particular mobile user may depend at least in part on the identity of the user stored in the database, and may also depend at least in part on a privilege level of the user stored in the database. For some users, the location-based triggering event is detection of the users' entry into the institutional space. Alternatively or in addition, the location-based triggering event is log-off of a user from an existing session.

The virtual desktop, when delivered, may include data from a previous session of the mobile user. In some embodiments, at least some of the data specifying session resources for the mobile user have been previously selected by the mobile user.

In another aspect, the invention pertains to a system for anticipatory provisioning of resources for a mobile user in an institutional space. In various embodiments, the system comprises a plurality of devices at different locations in the institutional space; a location server in operative communication with the devices via a network and including computer storage defining a user location database that itself includes records for a plurality of users, where each of the records includes, for one of the users, (i) data specifying a provisioning policy for the user including at least one location-based triggering event, and (ii) data indicative of a current location of the user; a desktop server in operative communication with the devices and the location server via the network, the desktop server including (i) a user desktop database that itself includes records for a plurality of users, each of the records specifying, for one of the users, session resources for the user and data indicative of a state of a user's previous session on one of the devices, (ii) a virtualization module for creating a virtual desktop including the session resources at the desktop server for remote session access and use at one of the devices via the network; and an authentication server for receiving user log-on credentials. Upon detection by the location server of a location-based triggering event for a user, the desktop server is configured to (i) responsively create the virtual desktop specified in the user desktop database for the user, and (ii) responsive to authentication of the user to the authentication server via one of the devices, provide network-based access to the virtual desktop at the device.

In some embodiments, the location-based triggering event is detection of user presence at a first location, and the location server is configured to predict a second location for the mobile user, where the second location is based on and different from the first location; and the desktop server is configured to deliver the virtual desktop to a device at the second location.

The location-based triggering events causing the delivery of the virtual desktop for a particular mobile user may depend at least in part on the identity of the user stored in the user location database, and may also depend at least in part on a privilege level of the user stored in the user location database. For some users, the location-based triggering event is detection of the users' entry into the institutional space. Alternatively or in addition, the location-based triggering event is log-off of a user from an existing session.

The desktop server may comprise storage for storing data from a user session and may be configured to create a new virtual desktop based on the stored data. The devices may comprise a desktop agent for receiving user selections of session resources and providing these, via the network, to the desktop server for inclusion in the user's record thereon.

In some embodiments, location server further comprises an action module for causing an additional action to take place at the second location. For example, the additional action may be one or more of setting a printer at the second location, bridging a USB device associated with the device at the second location, retrieving and displaying a census of patients at or near the second location, causing additional applications outside the virtual desktop to be launched at the device at the second location, or connecting and enabling dictation at the second location.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, routines, steps, or characteristics may be combined in any suitable manner in one or more examples of the technology. As used herein, the terms "approximately" and "substantially" mean ±10%, and in some embodiments, ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1:
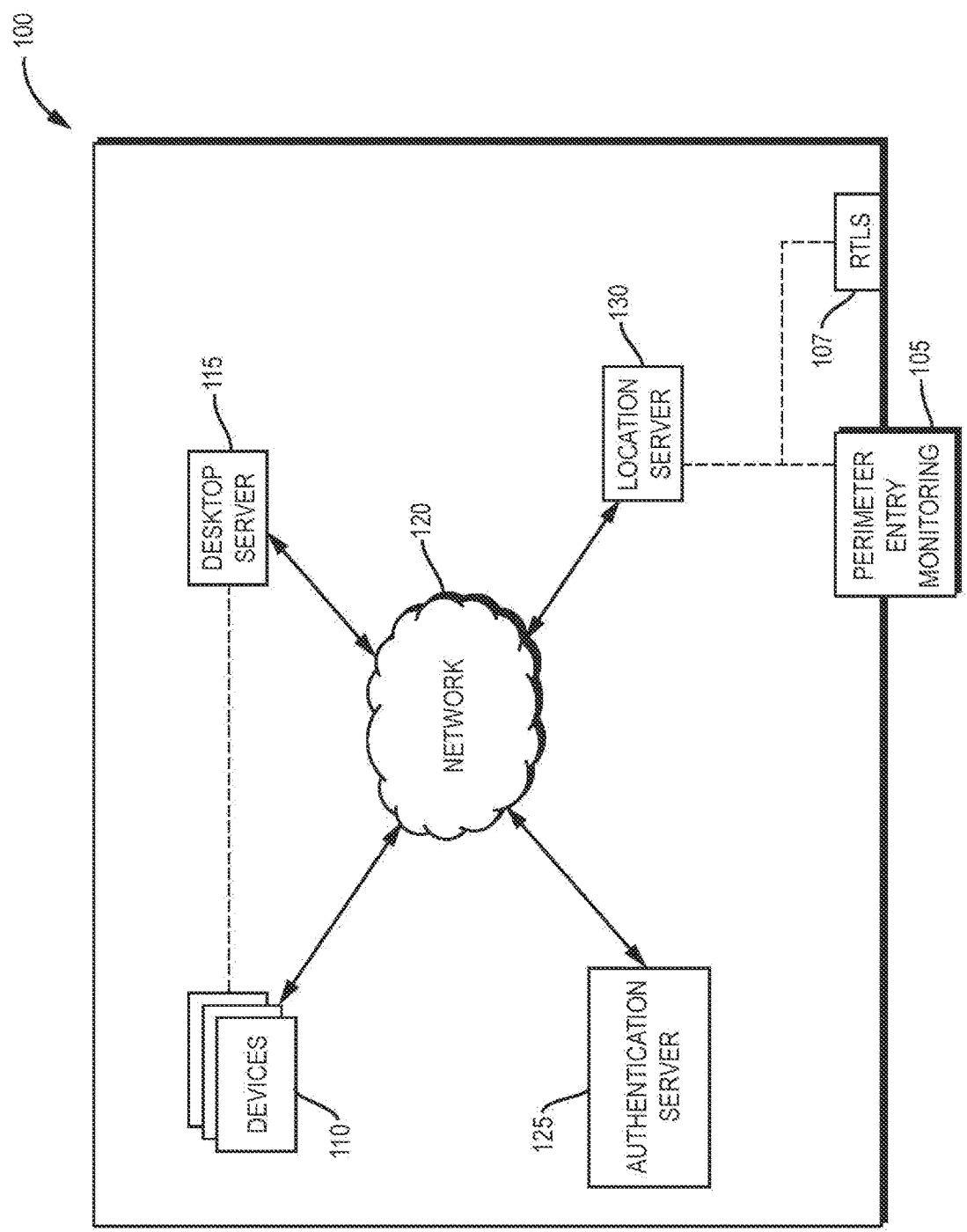
FIG. 1 schematically illustrates an institutional space including devices and servers in accordance with embodiments of the invention.

Refer first to FIG. 1, which illustrates a generalized environment in which embodiments of the invention may be deployed. The environment is an institutional space 100, such as a hospital, which may include multiple buildings each including perimeter-entry monitors 105. These may, for example, be card readers that detect and log user entry into the institution and/or restrict entry to secure areas to authorized personnel. An RTLS system 107 monitors the changing locations of users with the space 100 (e.g., via wireless detection of tags worn by users and/or affixed to devices they carry). A typically large number of devices 110, which may be movable within the space 100, are available for mobile users (i.e., clinicians who roam from place to place within the space 100) as they discharge their responsibilities. These devices 110, which include workstations, thick or thin client devices, kiosks, and network-connected medical devices are herein referred to collectively as "nodes." In general, a node is able to access, via a network, one or more data stores that include information (e.g., EMR) of interest to clinicians.

A desktop server 115 generates "virtual desktops" for users that are displayed on one of the devices 110 when the user logs in at that device. Particularly in secure environments or where sensitive data is accessed, many applications are not launched locally at the device 110 but are provided through a portal or "desktop agent," such as XENDESKTOP (supplied by Citrix Corp.) or the like, running on the device 110. The portal is in communication with desktop server 115 via a network 120. In a virtual-desktop environment, applications run within a hosted session generated on a secure, "locked-down" desktop server 115, which can create and maintain many simultaneous sessions at different devices 110. See, e.g., U.S. Pat. Nos. 8,866,701 and 9,009,219, the entire disclosures of which are hereby incorporated by reference.

Log-on may be handled by a separate (and conventional) authentication server 125, which authenticates users based on their credentials in accordance with an institutional security policy. That policy may require different tiers of authentication depending on the data to which the user seeks access; for example, a simple password log-in may be sufficient for access to routine applications, while a "strong" modality such as a biometric (e.g., fingerprint or vein) scan may be required for access to secure data.

A location server 130 maintains awareness of the locations of users within the space based on indicators such as the device on which the user's current session is active or, if the device location is unknown or no session is active, based on perimeter accesses and RTLS 207. RTLS reference points, which can be either transmitters or receivers, are spaced throughout a facility to detect the presence of identified tags.

The devices 110 and servers 115, 125, 130 communicate over the network 120. The term "network" is herein used broadly to connote wired or wireless networks of computers or telecommunications devices (such as wired or wireless telephones, tablets, etc.). For example, a computer network may be a local area network (LAN) or a wide area network (WAN). When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Networked computers may be connected over the Internet, an Intranet, Extranet, Ethernet, or any other system that provides communications. Some suitable communications protocols include TCP/IP, UDP, or OSI, for example. For wireless communications, communications protocols may include IEEE 802.11x ("Wi-Fi"), Bluetooth, Zigbee, IrDa, near-field communication (NFC), or other suitable protocol. Furthermore, components of the system may communicate through a combination of wired or wireless paths, and communication may involve both computer and telecommunications networks. For example, a user may establish communication with a server using a "smart phone" via a cellular carrier's network (e.g., authenticating herself to the server by voice recognition over a voice channel); alternatively, she may use the same smart phone to authenticate to the same server via the Internet, using TCP/IP over the carrier's switch network or via Wi-Fi and a computer network connected to the Internet.

It should also be understood that while the servers 115, 125, and 130 are shown as physically separate devices within the institutional space 100, this is for illustrative purposes only. Multiple servers may in fact reside on the same computer, and may be "virtualized." Moreover, even separate machines need not reside in the institution's on-site data center; many facilities, for example, contract with a third party for authentication services delivered "in the cloud," i.e., remotely over the Internet or the public telecommunications in a manner that is indistinguishable, to users, from a wholly local implementation. Accordingly, references herein to "servers" have no topological or device-level connotation; any functionally satisfactory deployment scheme, whether on a single or multiple machines wherever located, are within the scope of the present invention.

Figure 2:
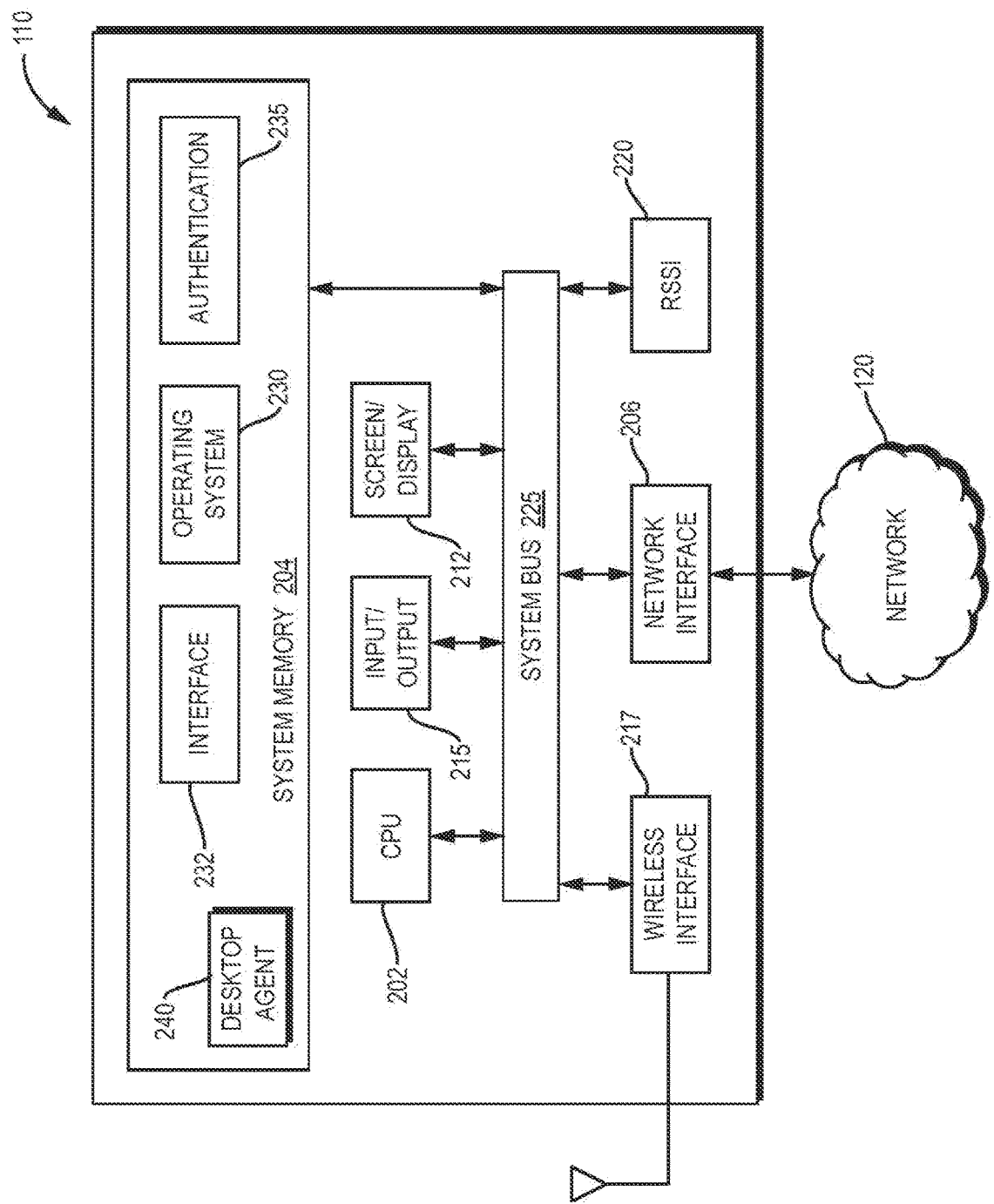
FIG. 2 schematically illustrates a node in accordance with embodiments of the invention.

FIG. 2 illustrates a representative node 110, which may be a workstation (e.g., a general-purpose personal computer running suitable software), a fat or thin client device, a kiosk, a network-connected medical device, or any other device with which clinicians and other users interact, and which may be moved from time to time within an institutional setting. Node 110 typically includes a processor 202 (e.g., a CPU microprocessor) and associated system memory 204, a network interface 206 (for connection to the institutional network 120 and/or the Internet), and, usually, one or more non-volatile digital storage elements (such as a hard disk, CD, DVD, USB memory key, etc.) and associated drives. Further, workstation 110 includes user input/output devices such as a display screen 212 and conventional tactile input devices 215 such as keyboard and mouse or touch pad. A wireless interface 217, which may be separate from or implemented within network interface 206, facilitates wireless communication with user mobile devices. In some embodiments, workstation 110 includes a received signal-strength indication (RSSI) circuit 220, which, again, may be implemented within or separate from the wireless interface 217. The various components communicate with each other via one or more buses 225.

In use, processor 202 executes one or more computer programs (conceptually illustrated as program modules) stored in system memory 204. An operating system 230 (such as, e.g., MICROSOFT WINDOWS, UNIX, LINUX, iOS, or ANDROID) provides low-level system functions, such as file management, resource allocation, and routing of messages from and to hardware devices (such as I/O device (s) 215) and one or more higher-level user applications (such as EMR applications, office programs, a web browser, etc.) An interface 232 generates screen displays and receives user input via the input devices, e.g., by the user's typing on the keyboard, moving the mouse, or clicking with the mouse on a displayed control element. In some implementations, node 110 includes an authentication agent 235 that allows a user to obtain access to restricted data consistent with his privilege level and the security policies of the institution. Authentication agents are known in the art and described, for example, in U.S. Ser. No. 11/294,354, filed Dec. 5, 2005, the entire disclosure of which is hereby incorporated by reference, and may communicate with a remote authentication server that securely stores user credentials. A desktop agent module 240 facilitates use of and interaction with remotely hosted applications via screen display 212, and also allows the user to modify settings on the application host server. For example, the user may specify or modify preferences, such as a set of default applications to be launched when a virtual desktop for the user is created.

Figure 3:
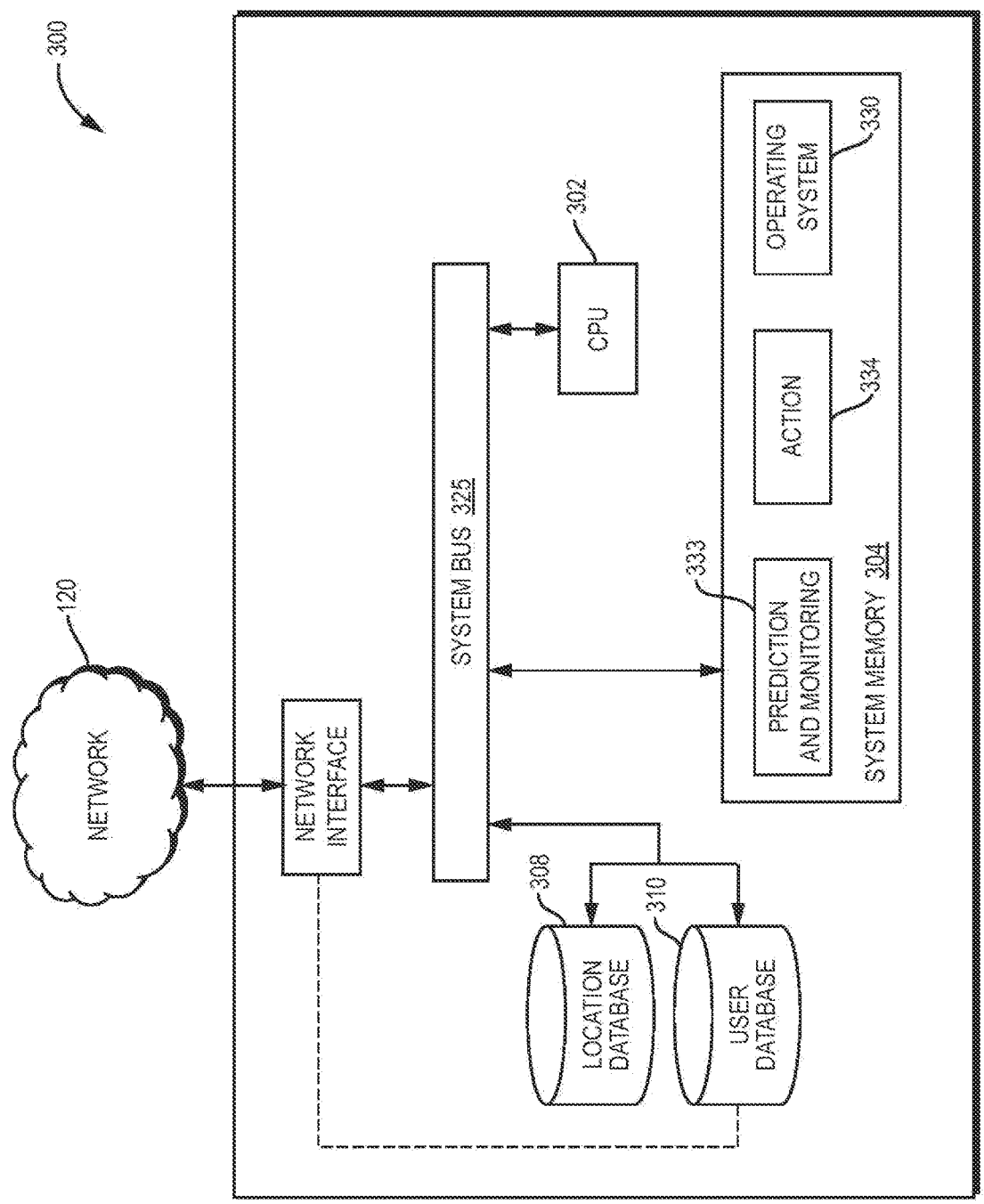
FIG. 3 schematically illustrates a location server in accordance with embodiments of the invention.

FIG. 3 illustrates a location server that also typically includes a processor 302 (e.g., a CPU) and associated system memory 304, a network interface 306, a system bus 325, and one or more non-volatile digital storage elements including a location database 308 and a user database 310. The databases 308, 310 may be stored locally as separate files or disk partitions, or may be stored remotely and accessed via network interface 306. Location database 308 stores records each specifying a node and its most recently determined physical location, and may also indicate its distance from other nodes. Database 310 stores records each specifying a user, location information for the user as described in greater detail below, a provisioning policy for the user, and, in some cases, a user privilege level. This dual-database arrangement provides flexibility in separating the task of keeping track of nodes from the task of keeping track of user activity and preferences—the former involving ongoing location awareness of nodes that may move and the latter involving ongoing awareness of current user activity and location. It should be stressed, however, that any number of databases, including a single database, may be used. Physical device locations may be obtained in any suitable fashion, e.g., entered once for fixed devices or reported by the devices or by others as devices are moved.

System memory 304 includes stored instructions defining an operating system 330. In addition, memory 204 stores a prediction and monitoring application 333 that, in various embodiments, predicts the next location of a user in response to a location-based triggering event (e.g., the detected departure of the user from a node), and an action module 334 that causes an action to be taken based on the triggering event. More generally, server 300 (as well as servers 125 and 115, which are conventional) may be implemented on any suitable computing platform including a processing unit, a system memory, and a system bus that couples various system components including the system memory to the processing unit. During operation, the system memory contains the instructions implementing the functionality described herein. Computers typically include a variety of computer-readable media that can form part of the system memory and be read by the processing unit. By way of example, and not limitation, the system memory may include computer storage media in the form of volatile and/or nonvolatile memory such as read only memory (ROM) and random access memory (RAM). A basic input/output system (BIOS), containing the basic routines that help to transfer information between elements, such as during start-up, is typically stored in ROM. RAM typically contains data and/or program modules that are immediately accessible to and/or presently being operated on by processing unit. The data or program modules may include an operating system, application programs, other program modules, and program data. The operating system may be or include a variety of operating systems such as Microsoft WINDOWS operating system, the Unix operating system, the LINUX operating system, the Xenix operating system, the IBM AIX operating system, the Hewlett Packard UX operating system, the MACINTOSH operating system, the APACHE operating system, an OPENSTEP operating system or another operating system of platform.

Desktop server 115 (see FIG. 1) may run one or more thin-client computing or remote display presentation applications. In one embodiment, server 115 executes as an application any portion of the CITRIX ACCESS SUITE by Citrix Systems, Inc., such as the METAFRAME or CITRIX PRESENTATION SERVER products, or applications such as CITRIX XENAPP, CITRIX XENDESKTOP, CITRIX ACCESS GATEWAY, and/or any of the MICROSOFT WINDOWS Terminal Services from Microsoft Corporation. As is conventional, desktop server 115 may maintain a default list of applications for each user (which list may be modified, either directly by the user or based on user activity) and session data. The session data enables a current session state to be fully replicated—i.e., each application as well as retrieved data are stored, either directly or (more commonly) as pointers, so that the user may continue a current session on a new virtual desktop launched, using the session data, on a different node. When the virtual desktop is created from the "golden image" (i.e., a master template), the current or default record data is used to deliver applications and retrieve data in accordance with the user's record in database 310.

Thus, a "virtual desktop," as that term is used herein, refers to a particular suite of applications launched by or otherwise delivered to a user, and data either typically or currently accessed by the user. In some circumstances, the virtual desktop represents the state of the user's current or most recent session on a node, including applications launched and user-requested data. In other circumstances, the virtual desktop is a representative session tailored to the particular user, either based on a registration sequence in which the user specifies applications to be launched at startup, or based on monitoring of user activity.

The current state of a user's hosted session is maintained in user database 310 and is easily updated, for example, by the desktop agent 240 resident on the user's current node 110 in response to a location-based triggering event. Desktop agent 240 monitors applications launched locally and remotely via the node 110, and adds identifiers for these applications to the user's record in user database 310. In addition, desktop agent 240 agent monitors data retrieved by the user (typically, though not necessarily, via one of the applications) and adds identifiers for these as well. For example, retrieved data may include documents opened in a word processor, patient records accessed via an EMR system, lab reports, real-time patient data obtained remotely from a medical device, etc. In some circumstances, the current data may be deleted and the default options reinstated—e.g., after a sufficiently long period has elapsed since session log-off that the prior session is unlikely to be relevant, or if the user has entered a different institutional facility. If the user has logged off from a session, or the session has timed out (i.e., has been deleted due to persistent inactivity), desktop server 115 will provision the user's default applications. If the user has not logged off, or has instructed desktop server 115 to save the current session, that session will be recreated for the user at the appropriate time—and just what time is appropriate may depend on various factors.

The timing of provisioning reflects a trade-off between use of system resources and the immediacy of a user's need for session access. The virtual desktop may be delivered on a node as soon as the user has logged on and authenticated himself at the node, or may not even be assembled until the user logs on. For minimal resource utilization, a user's default applications are not launched, or a current session is not regenerated at desktop server 115, until the user actually logs in. This minimal approach reflects common conventional practice. The latency experienced by a user may be reduced by instantiating a new (default) session or maintaining a current session on desktop server 115, so that when the user logs in at a new node, the virtual desktop has already been created and can be delivered there. For example, a default virtual desktop may be created at desktop server 115 when a user's presence is initially detected at the facility or, in some implementations, in a particular location (e.g., department). The latency experienced by the user is minimized when the virtual desktop is delivered to a predicted location and, when it becomes active, is hidden from view until the user logs in.

Following a location-based triggering event, the user's record in user database 310 is updated, and is updated again the next time the user is detected at a monitored location. As noted above, the user's current location may be based on indicators such as the device on which the user's current session is active or, if the device location is unknown or no session is active, based on perimeter accesses and RTLS. To support the operation of prediction and monitoring module 333, user database 310 may maintain a history of sequentially detected user locations, e.g., over the course of a day or longer period.

A location-based triggering event can be any detectable event suggesting a user change of location. For example, when a user logs off a current session, or if a "walk-away" event is detected at the user's current node (as described, for example, in U.S. Pat. No. 8,538,072, the entire disclosure of which is hereby incorporated by reference), a triggering event may be recorded by module 333; more specifically, in the illustrated embodiment, the current node reports the log-off or walk-away event to location server 300, and module 333 both updates the user record in database 310 to reflect an unknown current user location and takes action based on the provisioning policy in the user record. Other location-based detection events can include log-in at a device other than that listed as the user's current device in user database 310 (indicating that the user has departed from the listed device without logging off or having the departure detected), or presence detection at a location different from the location of the device listed as the user's current device in user database 310. More generally, any event associating the user with a current location—e.g., passing through perimeter security, having an access card or user-associated mobile device detected by a reader, etc.—can be detected and reported to module 333. Depending on the provisioning policy associated with the user, such events may only have significance (i.e., cause an action to take place) if a current user device and/or desktop server 115 reports the user as having logged on via authentication server 125. In this way, resources are not committed for users who have not yet begun sessions and/or authenticated themselves. For some users, however, mere detection may cause a virtual desktop to be created. For example, for some personnel (e.g., surgeons and supervisory personnel), the virtual desktop may be created as soon as the individual's presence within a facility is detected, e.g., by perimeter entry system 105, or when s/he is detected (e.g., by a beacon or RTLS 107) near a particular location within the facility. These location criteria and associated actions are stored in the provisioning policy field of the user's record in database 310, e.g., as a privilege level.

With reference to FIGS. 1-3, in a representative operational sequence, location server 300 registers a location-based triggering event involving a user. In response, module 333 retrieves from user database 310 the provisioning policy associated with the user. Module 333 may signal desktop server 115 to save the current session state of the user; for example, module 333 may retrieve from database 310 the identifier of the device at which the triggering event was detected and instruct desktop server 115 to save the current session state at this device (and, in some cases, also to terminate the session to avoid unwanted visibility of sensitive data on the device display) and/or to maintain the user's virtual desktop so that it may be accessed directly from a different device (following user authentication thereon).

Module 333 may predict the next location or device where the user is expected to appear. In some embodiments, module 333 uses a simple rule base to predict the node that a user is most likely to use next. Such an approach is feasible where user activity tends to follow established patterns. For example, if module 333 detects that a surgeon has just departed a hospital's imaging department after viewing a patient's CAT scan, it may query a hospital information server for the current location and status of the patient whose scan was being viewed. If the patient is scheduled for surgery, module 333 may query location database 308 to determine the device closest to the surgical suite where the patient is expected to soon arrive, and instruct desktop server 115 to deliver a virtual desktop to this device and recreate thereon the saved user session.

If actions beyond instructing the desktop server 115 to deliver a virtual desktop are contemplated, they may be executed by the dedicated action module 334. For example, in response to a triggering event, action module 334 may cause commands to be sent via network interface 206 to set the closest printer associated with the target device where the virtual desktop will be delivered; bridge USB devices associated with the target device so they can be accessible by the hosted session when the user arrives at the target device; retrieve and display a census of the patients on the floor that the provider needs to see; cause additional applications outside the virtual desktop to be launched at the target device or at a neighboring or connected device; and connecting and enabling dictation at the target location.

Module 333 may also base a location prediction on past activity and/or correlations between application use and subsequent activities, using, for example, conventional unsupervised learning or neural-net techniques. In these embodiments, a location history maintained for each user in database 310 is used to update the predictive model. For example, the user's daily monitored movements may be used to update the model at the end of a day.

The timing of creation and delivery may depend on the identity of the user and the degree of confidence in a prediction. In some embodiments, virtual desktops are assembled and, in some cases, delivered to a node in advance for users who, for example, frequently move among nodes; such users would otherwise repeatedly suffer start-up delays as virtual desktops are prepared, and the commitment of additional computational resources to prepare the desktop in advance is merited for such users. A user's priority determining whether a virtual desktop is prepared in advance may depend on a privilege level associated with the user in database 310. For high-priority users, the virtual desktop may be prepared as soon as the user's entry into the facility has been registered, and it may be delivered to the node that the user is likely to access first (e.g., based on past history). After these high-priority users have logged in, a location-based triggering event indicative of departure from a node may be sufficient to cause delivery of a virtual desktop to a predicted next node; while for lower-priority users, a second location-based triggering event indicative of arrival at a node is necessary to cause delivery of the virtual desktop to that node.

In some embodiments, the virtual desktop is not created (or delivered to the predicted next node) unless a sufficiently high confidence level is registered (or unless the user's privilege level is sufficiently high). The confidence level may be based on various factors—most simply, the user's history of movement patterns among nodes. However, the desktop server may consider corroborating factors tending to reinforce the prediction (in a manner analogous to optimistic caching). For example, if, having walked away from node A, past activity patterns (of the particular user or generally among users) suggest the user will next log on at node B, the confidence level is increased if RTLS detects the user in proximity to node B or predicts a trajectory encompassing node B. Setting up the virtual desktop at this point of prediction rests on a relatively high confidence level that the operations will not be wasted, and occurs sufficiently in advance of the user's actual arrival at node B to avoid set-up delay when the user logs on. Conversely, delivery may be suspended if the predicted node is currently in use by someone else, or delivery may be shifted to a nearby node (particularly if there are no other nodes in the vicinity). If the user passes the predicted node without stopping, the virtual desktop may be revoked from the predicted node, at which point the desktop server may predict a new destination for the user. In this context, revocation generally means that the provisionally established connection between the virtual desktop and the predicted device is broken.

Preferably, it is the user's physical destination, rather than the identifier of a particular device that can be moved, which is predicted. Records in location database 308 associate a predicted destination with the device currently at that location.

Any suitable programming language may be used to implement without undue experimentation the functions described above, including those of desktop agent 240 and prediction and monitoring module 333, with processing responsibility allocated between node 110 and servers 115, 130 as desired by the system designer. Illustratively, the programming language used may include assembly language, Ada, APL, Basic, C, C++, C*, COBOL, dBase, Forth, FORTRAN, Java, Modula-2, Pascal, Prolog, Python, REXX, and/or JavaScript, for example. Further, it is not necessary that a single type of instruction or programming language be utilized in conjunction with the operation of the system and method of the invention. Rather, any number of different programming languages may be utilized as is necessary or desirable.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method of anticipatory provisioning of resources for mobile users in an institutional space, the method comprising:
   detecting entry of a mobile user into the institutional space;
   after detecting entry of the mobile user, (i) predicting a first physical destination, within the institutional space, at which the mobile user is likely to arrive, and (ii) causing a virtual desktop for the mobile user to be created within a hosted session at a server;
   determining if a first network-connected node is disposed at the first physical destination, the first network-connected node being movable within the institutional space;
   when the first network-connected node is disposed at the first physical destination, delivering the virtual desktop to the first network-connected node prior to arrival of the mobile user at the first network-connected node; and
   after arrival of the mobile user at the first network-connected node, receiving authentication credentials for the mobile user, and, upon acceptance of the authentication credentials for the mobile user, providing network-based access for the mobile user to the virtual desktop at the first network-connected node.

2. The method of claim 1, further comprising:
   detecting an electronically detected location-based triggering event indicative of departure of the mobile user from the first network-connected node; and
   in response to the electronically detected location-based triggering event indicative of departure of the mobile user from the first network-connected node, (i) predicting a second physical destination, within the institutional space and different from the first physical destination, at which the mobile user is likely to arrive, (ii) determining if a second network-connected node is disposed at the second physical destination, and (iii) when the second network-connected node is disposed at the second physical destination, delivering the virtual desktop to the second network-connected node.

3. The method of claim 2, wherein the second network-connected node is movable within the institutional space.

4. The method of claim 2, wherein the virtual desktop is delivered to the second network-connected node before arrival of the mobile user at the second network-connected node.

5. The method of claim 2, further comprising:
   after arrival of the mobile user at the second network-connected node, receiving authentication credentials for the mobile user, and, upon acceptance of the authentication credentials for the mobile user, providing network-based access for the mobile user to the virtual desktop at the second network-connected node.

6. The method of claim 2, further comprising, after arrival of the mobile user at the second network-connected node, providing network-based access for the mobile user to the virtual desktop at the second network-connected node without requiring additional authentication from the mobile user.

7. The method of claim 2, wherein the second physical destination is predicted based at least in part on information accessed by the mobile user at the first network-connected node.

8. The method of claim 7, wherein the information comprises patient information.

9. The method of claim 2, wherein the second physical destination is predicted based on a location history, within the institutional space, of the mobile user.

10. The method of claim 1, wherein the entry of the mobile user into the institutional space is detected using a perimeter-entry monitoring system.

11. The method of claim 1, wherein the first physical destination is predicted based on a location history, within the institutional space, of the mobile user.

12. The method of claim 1, wherein the virtual desktop comprises data from a previous session of the mobile user.

13. The method of claim 1, wherein the virtual desktop, when delivered, includes (i) data from a previous session of the mobile user when a default-restoration triggering event has not occurred prior to creation of the virtual desktop, or (ii) default data for the mobile user when the default-restoration triggering event has occurred prior to creation of the virtual desktop.

14. The method of claim 13, wherein the default-restoration triggering event comprises a log-off by the mobile user from the previous session.

15. The method of claim 13, wherein the default-restoration triggering event comprises a period of inactivity associated with the previous session of the mobile user.

16. The method of claim 1, wherein determining if the first network-connected node is disposed at the first physical destination comprises consulting a database containing records associating network-connected nodes movable within the institutional space with their current physical locations.

17. The method of claim 1, wherein the first network-connected node comprises a workstation, a fat or thin client device, a kiosk, or a network-connected medical device.

\* \* \* \* \*